(12) United States Patent
Mao et al.

(10) Patent No.: US 9,933,356 B2
(45) Date of Patent: Apr. 3, 2018

(54) APPARATUS AND METHOD FOR DETECTING AND ANALYZING MACROMOLECULES IN BIOLOGICAL FLUID

(71) Applicant: Shanghai Lexvu Opto Microelectronics Technology Co., Ltd, Shanghai (CN)

(72) Inventors: Jianhong Mao, Shanghai (CN); Fengqin Han, Shanghai (CN); Shan Huang, Shanghai (CN)

(73) Assignee: SHANGHAI JADIC OPTOELECTRONICS TECHNOLOGY CO., LTD., Shanghai (CN)

( * ) Notice: Subject to any disclaimer, the term of this patent is extended or adjusted under 35 U.S.C. 154(b) by 253 days.

(21) Appl. No.: 14/722,582

(22) Filed: May 27, 2015

(65) Prior Publication Data
US 2015/0346082 A1    Dec. 3, 2015

(30) Foreign Application Priority Data
May 28, 2014  (CN) .......................... 2014 1 0230627

(51) Int. Cl.
  *G01N 21/17*    (2006.01)
  *G01N 33/487*   (2006.01)
  *G01D 5/34*     (2006.01)
  *G01N 21/59*    (2006.01)
  *G01N 21/03*    (2006.01)

(52) U.S. Cl.
  CPC .............. *G01N 21/17* (2013.01); *G01D 5/34* (2013.01); *G01N 21/59* (2013.01); *G01N 33/487* (2013.01); *G01N 21/03* (2013.01); *G01N 2021/0346* (2013.01)

(58) Field of Classification Search
  CPC ............................ G01N 21/17; G01N 33/487
  USPC .......................................................... 250/564
  See application file for complete search history.

(56) References Cited

U.S. PATENT DOCUMENTS

| 7,595,883 | B1 * | 9/2009 | El Gamal | ......... B01L 3/502715 356/246 |
| 2004/0264903 | A1 * | 12/2004 | Dridi | ....................... B82Y 20/00 385/129 |
| 2008/0099698 | A1 * | 5/2008 | Rahman | ................. B82Y 20/00 250/493.1 |

* cited by examiner

*Primary Examiner* — Seung C Sohn
(74) *Attorney, Agent, or Firm* — Muncy, Geissler, Olds & Lowe, P.C.

(57) ABSTRACT

An apparatus for detecting macromolecules in a biological fluid is discloses which includes a first substrate and a second substrate. The first substrate includes a plurality of sampling apertures, at least some of which have different diameters. The sampling apertures are configured to screen and isolate the macromolecules in the biological fluid. The second substrate is stacked with the first substrate and includes a plurality of detectors vertically corresponding in position to the sampling apertures. Each of the detectors is configured to detect whether one of the macromolecules is present in a corresponding one of the sampling apertures and produce a detection output signal. A method for detecting macromolecules in a biological fluid is also disclosed. The apparatus has high integration and simple manufacturability, while the method is easy to use.

4 Claims, 5 Drawing Sheets

APPARATUS AND METHOD FOR DETECTING AND ANALYZING MACROMOLECULES IN BIOLOGICAL FLUID

CROSS-REFERENCES TO RELATED APPLICATIONS

This application claims the priority of Chinese patent application number 201410230627.6, filed on May 28, 2014, the entire contents of which are incorporated herein by reference.

TECHNICAL FIELD

The present invention provides apparatuses and methods for detecting macromolecules in a biological fluid and relates to the field of system design, processing, packaging, and applications of semiconductor biochips.

BACKGROUND

Accurate early-stage diagnosis of some severe diseases associated with high morbidity and mortality rates, including cancers and heart diseases, is very difficult. Existing diagnostic technologies typically depend on macro data and information, such as body temperature, blood pressure and scanned body images. Many common diagnostic instruments based on imaging technologies, including X-ray, CT scan, nuclear magnetic resonance (NMR), have been used in the detection of serious diseases such as cancers. Although these technologies can make contributions to various extents to disease detection, most of these technologies cannot achieve accurate, completely safe and low-cost early-stage diagnosis for severe diseases such as cancers. In addition, many existing diagnostic technologies and related instruments are invasive and sometimes rarely available, particularly in remote and rural areas.

Currently, detection, particularly DNA detection, of various macromolecules in biological fluids, that can provide crucial biological and pathological information, has become an important tool in regular physiological testing for identification of disease causes, pathogen analysis and genetic research.

In the field of detection of various macromolecules in biological fluids, efforts have been focused on how to perform such detection in a fast, reliable, accurate and economical manner to provide more timely biological and pathological information for the diagnosis and detection of diseases. In recent years, there have been some efforts to introduce the nano-technology to a variety of biological applications, most of which are about the gene mapping and mild disease detection. For example, some scholars have discussed the use of micro-electro-mechanical systems (MEMS) sensors in in-vitro detection of cancer cells in blood and bone marrow, and there has also been disclosed by a scholar in the United States a method of MEMS-based detection of a biological medium.

However, all such detection methods involve complex sample preparation procedures (e.g., the use of chemical or biological markers) which lead to a complicated and time-consuming detection process, making these approaches unsuitable for real-time diagnosis of serious diseases such as cancers, especially for conventional hospital screening and regular physical examination.

In order to address this issue, the present invention provides apparatuses and methods for detecting a macromolecule in a biological fluid, which employ a silicon micromachining technology to integrate a silicon sieve for the macromolecules, silicon semiconductor detectors and even a detection signal processor, and thus provide the advantages such as high integration, simple manufacturability, convenience in use, high detection and signal processing accuracy and high speed.

SUMMARY OF THE INVENTION

The present invention seeks to improve the miniaturization, integration, digitalization and process standardization of systems for detecting macromolecules in biological fluids.

To this end, the present invention proposes an apparatus for detecting macromolecules in a biological fluid, including:

a first substrate, including a plurality of sampling apertures, at least some of the plurality of sampling apertures having different diameters, the plurality of sampling apertures configured to screen and isolate the macromolecules in the biological fluid; and a second substrate, stacked with the first substrate and including a plurality of detectors vertically arranged in correspondence with positions of the plurality of sampling apertures, each of the plurality of detectors configured to detect whether one of the macromolecules is present in a corresponding one of the plurality of sampling apertures and produce a detection output signal.

Optionally, the plurality of detectors may be photoelectric detectors.

Optionally, the second substrate may be a semiconductor substrate, and the photoelectric detectors may be semiconductor photoelectric detectors.

Optionally, the second substrate may be a silicon semiconductor substrate.

Optionally, each of the photoelectric detectors may include at least a photoelectric diode having a light-receiving surface facing toward a corresponding one or corresponding ones of the plurality of sampling apertures.

Optionally, each of the photoelectric detectors may further include a first switching transistor and a second switching transistor, wherein:

the first switching transistor has a drain coupled to a first end of the photoelectric diode, a gate coupled to a reset control signal and a source receiving a reset input signal, and a second end of the photoelectric diode is connected to a common ground; and the second switching transistor has a gate coupled to the first end of the photoelectric diode and the drain of the first switching transistor, a source coupled to an amplified input signal, and a drain outputting a corresponding detection output signal.

Optionally, each of the photoelectric detectors may further include a third switching transistor, wherein:

the third switching transistor has a source coupled to the first end of the photoelectric diode, a gate coupled to an inductive conducting and reset control signal, and a drain coupled to both the drain of the first switching transistor and the gate of the second switching transistor.

Optionally, the plurality of detectors may be thermal radiation detectors.

Optionally, the plurality of detectors may be radio frequency (RF) signal detectors.

Optionally, the apparatus may further include a collection analysis module configured to receive the detection output signals from the plurality of detectors and identify properties of the macromolecules based on the received detection output signals.

Optionally, the apparatus may further include a detection source signal transmission module configured to transmit detection source signals toward the first substrate and the macromolecules retained in the plurality of sampling apertures, wherein the plurality of sampling apertures generate output sampling response signals in response to the detection source signals and the plurality of detectors sense the output sampling response signals and produce the detection output signals.

Optionally, a gap may be formed between the first substrate and the second substrate.

Optionally, the first substrate and the second substrate may be attached together by a plurality of separate adhesive pads or by a continuous adhesive pad with an opening such that the gap is formed between the plurality of sampling apertures and the plurality of detectors.

Optionally, the plurality of sampling apertures may have at least twenty different diameters ranging from 0.1 μm to 100 μm.

Optionally, the first substrate may be a silicon semiconductor substrate having a thickness of from 1 μm to 750 μm.

Optionally, the first substrate may be a silicon substrate.

Optionally, the sampling apertures may be distributed in the first substrate in an array and the diameters of the plurality of sampling apertures increase or decrease successively row-by-row or column-by-column.

Optionally, the plurality of detectors may be arranged in parallel and have ends arranged on a planar surface of the second substrate, each of the plurality of sampling apertures in the first substrate vertically corresponding to one of the plurality of detectors.

According to another aspect, the present invention also provides a method for detecting macromolecules in a biological fluid, which uses an apparatus as defined above. The method includes:

screening and isolating the macromolecules in the biological fluid by means of the plurality of sampling apertures in the first substrate, such that the macromolecules are filled and retained in corresponding ones of the plurality of sampling apertures having diameters matching sizes of the macromolecules;

applying detection source signals to the first substrate;

converting the detection source signals into sampling response output signals by transmitting the detection source signals through the plurality of sampling apertures;

detecting the sampling response output signals and outputting detection output signals by the plurality of detectors in the second substrate that vertically correspond to the plurality of sampling apertures in the first substrate; and processing the detection output signals to obtain properties of the macromolecules in the biological fluid.

Optionally, the method may further include:

performing a temperature control on the first substrate and the macromolecules retained in the plurality of sampling apertures in the first substrate.

Optionally, the temperature control performed on the first substrate and the macromolecules retained in the plurality of sampling apertures in the first substrate may be accomplished by increasing or decreasing a temperature of the second substrate.

Optionally, the temperature control performed on the first substrate and the macromolecules retained in the plurality of sampling apertures in the first substrate may be accomplished by directly increasing or decreasing a temperature of the first substrate.

Optionally, the temperature of the first substrate and the macromolecules retained in the plurality of sampling apertures may range from −196° C. to 99° C.

Compared to the conventional solutions, in the apparatuses and methods according to the present invention: a first substrate includes a plurality of sampling apertures configured to screen and isolate macromolecules in a biological fluid, at least some of which vary in diameter; and a second substrate is stacked with the first substrate and includes a plurality of detectors, vertically corresponding in position to the sampling apertures, each of which is configured to detect whether one of the macromolecules is present in a corresponding one of the sampling apertures and produce a detection output signal.

During the detection, the first substrate serves as a macromolecular sieve to screen and isolate the macromolecules by means of the sampling apertures. After the macromolecules are retained in the correspondingly-sized sampling apertures, the second substrate functions as a detector array to produce different detection output signals by detectors depending on whether the respective sampling apertures retain one of the macromolecules or not. On the basis of these detection output signals, properties of the macromolecules in the biological fluid are analyzable and predictable.

Therefore, the apparatuses according to the present invention provide advantages such as a miniaturized system, high manufacturability and high integration, while the methods according to the invention are highly objective and easy to use.

BRIEF DESCRIPTION OF THE DRAWINGS

The following drawings are included herein as part of the present invention for a better understanding of the invention. The drawings illustrate embodiments of the present invention as well as their description, intended for explaining the principles of the invention.

In these drawings.

DETAILED DESCRIPTION

An apparatus for detecting macromolecules in a biological fluid according to an embodiment of the present invention will be described in detail below with reference to FIGS. 1 and 2. Apparatuses and methods according to embodiments of the present invention can be used in various bioassays, including the detection of the biological properties of DNA molecules contained in biological fluids.

Figure 1:
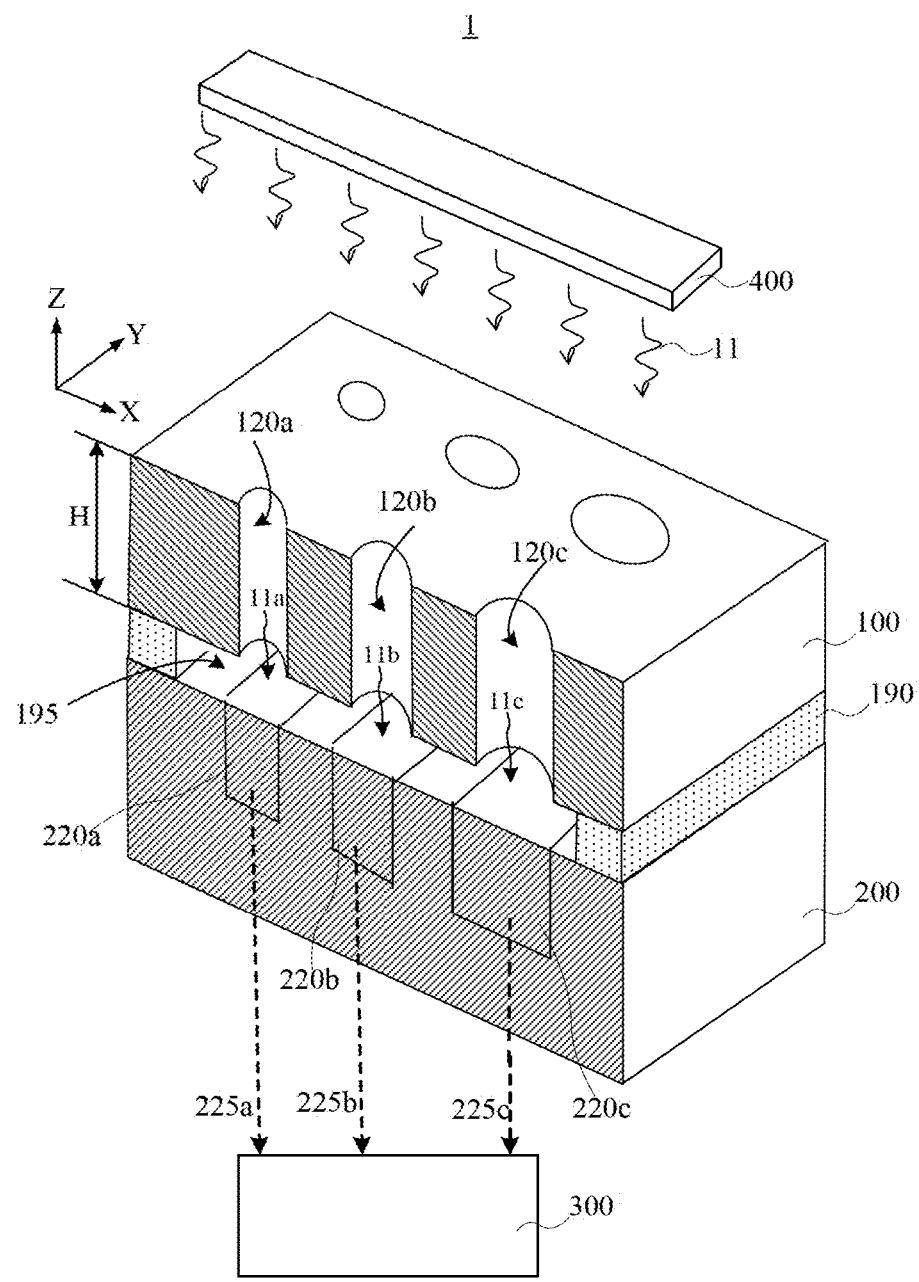
FIG. 1 is a schematic illustrating an apparatus for detecting macromolecules in a biological fluid according to one embodiment of the present invention.

Referring to FIG. 1, the apparatus 1 for detecting macromolecules in a biological fluid includes a first substrate 100 and a second substrate 200 arranged in a stacked manner. Preferably, there is a gap 195 formed between the first substrate 100 and the second substrate 200.

The first substrate 100 includes a plurality of sampling apertures, at least some of these sampling apertures vary in diameter. These sampling apertures are configured to screen and isolate the macromolecules in the biological fluid. Preferably, the first substrate 100 is fabricated from a semiconductor material. Preferably, the first substrate 100 is a silicon semiconductor substrate. In this case, the sampling apertures are accordingly silicon sampling apertures. Alternatively, the first substrate 100 may also be a silicon germanium semiconductor substrate, a germanium semiconductor substrate, a zinc oxide substrate or any other suitable substrate for screening the macromolecules, which are also within the scope of the present invention. Preferably, the first substrate 100 has a thickness H in the range from 1 μm to 750 μm, for example, 1 μm, 5 μm, 10 μm, 20 μm, 50 μm, 100 μm, 200 μm, 300 μm, 400 μm, 500 μm, 600 μm or 700 μm, such that the sampling apertures each have a depth suitable for screening the macromolecules which are held in, but will not drop out of, the respective sampling apertures sized correspondingly to the macromolecules.

Figure 2:
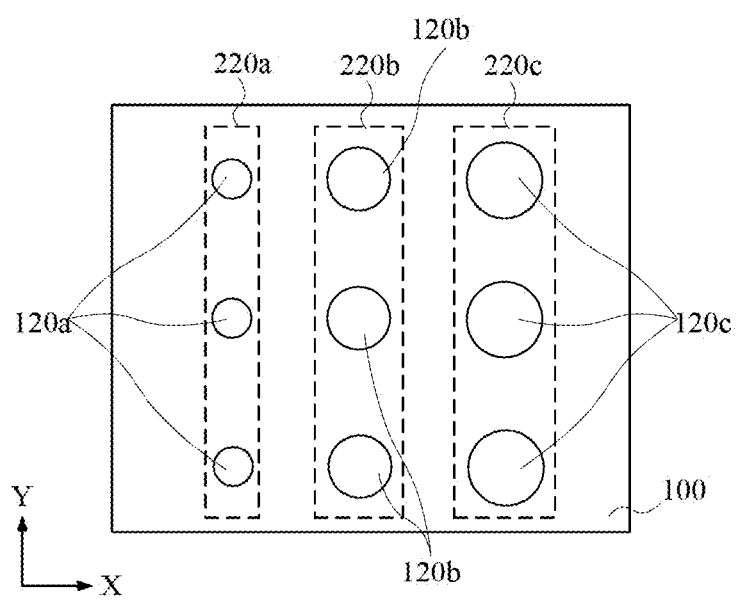
FIG. 2 is a top view of an apparatus for detecting macromolecules in a biological fluid according to one embodiment of the present invention.

Referring to FIG. 2, it is to be noted that the number of distinct diameters of the sampling apertures of the first substrate 100 depends on properties of the biomolecules being screened. Since the apparatus according to this embodiment is provided for the screening of DNA molecules, the diameters of the sampling apertures are desirably related to dimensional properties of the DNA molecules. As molecules in human DNA are of about twenty distinct diameters, the number of different diameters of the sampling apertures in this embodiment is accordingly about twenty and the aperture diameters correspond to the respective DNA molecule diameters. That is, the diameter of each sampling aperture matches the diameter of a corresponding one of the macromolecules such that the macromolecules can snugly fit into the corresponding aperture diameters. For the sake of illustrative and descriptive convenience, the following description is made with reference to an example in which the first substrate 100 includes sampling apertures 120a, 120b and 120c of three different diameters.

In this example, the sampling apertures 120a, 120b and 120c are distributed in the first substrate 100 in an array and the diameters of the sampling apertures 120a, 120b and 120c increase successively. With a first direction X as a direction of rows of the array and a second direction that is perpendicular to the first direction as a direction of columns of the array, sampling apertures in each of the column have the same diameter and sampling apertures in each of the row have their diameters increasing successively. That is, the sampling apertures 120a are arranged in a same column (the first column), the sampling apertures 120b are arranged in a same column (the second column), and the sampling apertures 120c are arranged in a same column (the third column); and in each row, a sampling aperture 120a, a sampling aperture 120b and a sampling aperture 120c is arranged in this order. Such configuration is conducive to improving the reliability in the screening of the macromolecules. While the first substrate 100 has been described above as including sampling apertures of three different diameters, the present invention is not limited in this regard as in other embodiments the first substrate 100 may also include sampling apertures of two, four, five, six or more different diameters depending on specific properties of the macromolecules in the fluid.

Additionally, while the sampling apertures have been described above as being arranged in three rows, the present invention is not limited in this regard as in other embodiments the sampling apertures may also be arranged in one, two, four, five or more rows. In general terms, the greater the number of the rows of the sampling apertures is, the higher the screening reliability of the macromolecules will be. Similarly, while the sampling apertures have been described above as being arranged in three columns, the present invention is not limited in this regard as in other embodiments the sampling apertures may also be arranged in one, two, four, five or more columns. Generally, the greater the number of the columns of the sampling apertures is, the higher the screening reliability of the macromolecules will be. Further, the present invention is not limited to the above-described arrangement of the sampling apertures. Rather, sampling apertures in each row and/or column can have the same diameter or different diameters which increase or decrease successively.

Preferably, each of the diameters of the sampling apertures is in the range of from 0.1 μm to 100 μm such as, for example, 0.5 μm, 1 μm, 5 μm, 10 μm, 20 μm, 30 μm, 40 μm, 50 μm, 80 μm or any other value compatible with the size of a DNA molecule to be screened. Preferably, the first substrate 100 includes at least twenty of the sampling apertures each having a different diameter. That is, in order to obtain a high screening accuracy, the sampling apertures in the first substrate 100 have at least twenty different diameters for retaining DNA molecules of various sizes. It will be understood by those skilled in the art that in case of the macromolecules being non-human DNA molecules, such as animal DNA molecules, for example, cat DNA molecules, the number of distinct diameters of the sampling apertures may match the number of types of the animal DNA molecules, and each of the distinct diameters of the sampling apertures may match the size of one of the animal DNA molecules of a corresponding type.

As shown in FIG. 1, the second substrate 200 is stacked with the first substrate 100. Preferably, the second substrate 200 is made of a semiconductor material. Preferably, the second substrate 200 is a silicon semiconductor substrate. Alternatively, the first substrate 100 may also be a silicon germanium semiconductor substrate, a germanium semiconductor substrate, a zinc oxide substrate or the like. The second substrate 200 includes a plurality of detectors each vertically aligned with a corresponding one of the plurality of sampling apertures to detect whether one of the macromolecules is present in the corresponding one of the plurality of sampling apertures. In this embodiment, the second substrate 200 includes detectors 220a, 220b and 220c which are located on a side of the second substrate 200 facing the first substrate 100 such that each of the sampling apertures corresponds to one of the detectors 220a, 220b and 220c.

In this embodiment, the detectors 220a, 220b and 220c each has an end arranged in parallel on a planer surface of the second substrate 200. Sampling apertures in each column have the same diameter and collectively vertically correspond to one of the detectors. This is advantageous in reducing the number of the detectors used, facilitating the arrangement of the detectors in the second substrate 200 and simplifying the fabrication process of the second substrate 200. In an alternative embodiment, sampling apertures in each column have the same diameter and each vertically correspond to one of the detectors.

As shown in FIG. 2, each of the detectors 220a, 220b and 220c is a stripe, and the sampling apertures 120a in the first column correspond to the detector 220, the sampling apertures 120b in the second column to the detector 220b, and the sampling apertures 120c in the third column to the detector 220c. While the sampling apertures 120a, 120b and 120c have been described above as being arranged in the first substrate 100 in an array, the present invention is not limited in this regard as the sampling apertures can be arranged in a disorderly manner in the first substrate 100. In addition, each of the sampling apertures may correspond to a dedicated one of the detectors. That is, the sampling apertures and the detectors are provided in one-to-one correspondence, which is also within the scope of the present invention.

Preferably, a detection source signal transmission module 400 may transmit detection source signals 11 to the first substrate 100 as well as the macromolecules contained in the sampling apertures. The sampling apertures may produce sampling response output signals 11' in response to the detection source signals. The detectors may sense the sampling response output signals 11' and output detection output signals.

As shown in FIG. 1, in this embodiment, the detection source signals 11 are applied from a side of the first substrate 100 opposite to the second substrate 200. The sampling response output signals 11a, 11b, 11c are the detection source signals 11 that have passed through the sampling apertures. In case of the macromolecules not present in the sampling apertures 120a, 120b and 120c, the detection source signals 11 pass through the sampling apertures 120a, 120b and 120c and then form the sampling response output signals 11a, 11b, 11c. Afterwards, the detectors 220a, 220b and 220c respectively receive the sampling response output signals 11a, 11b, 11c which pass through the sampling apertures 120a, 120b and 120c and then subsequently output the detection output signals 225a, 225b and 225c. In case of the macromolecules present in the sampling apertures 120a, 120b and 120c, the detection source signals 11 are attenuated by the macromolecules. The attenuated detection source signals 11 pass through the sampling apertures 120a, 120b and 120c and then form the sampling response output signals 11a, 11b, 11c. In this embodiment, the detection source signals 11 are visible light beams emanated from the detection source signal transmission module 400. In an alternative embodiment, the detection source signal transmission module 400 may not be included and the detection source signals 11 may be light beams directly generated by a light source. In this case, the light source may directly apply the detection source signals 11 from the side of the first substrate 100 opposite to the second substrate 200.

While the detection source signals 11 have been described above as being applied from the side of the first substrate 100 opposite to the second substrate 200, the present invention is not limited to this regard, as in other embodiments, the detection source signals 11 may also be applied from a side of the first substrate 100 facing the second substrate 200. In this case, for example, the detection source signal transmission module 400 may be arranged on the second substrate 200 or in the gap 195 and emit the detection source signals 11 toward the sampling apertures 120a, 120b and 120c, and the sampling response output signals may be the signals that are reflected from the macromolecules in the sampling apertures 120a, 120b and 120c. As a result, in case of the macromolecules not present in the sampling apertures 120a, 120b and 120c, the detection source signals 11 will pass through the sampling apertures 120a, 120b and 120c directly and the detectors 220a, 220b and 220c will not receive any sampling response output signal; and in case of the macromolecules present in the sampling apertures 120a, 120b and 120c, upon the detection source signals 11 directly reaching the sampling apertures 120a, 120b and 120c, the detection source signals 11 will be reflected thereby and form the sampling response output signals subsequently received by the detectors 220a, 220b and 220c which responsively produce the detection output signals 225a, 225b and 225c.

As shown in FIG. 1, the sampling apertures 120a, 120b and 120c are all oriented in a third direction Z that is perpendicular to a plane X-Y. The detection source signals 11 travel in the sampling apertures 120a, 120b and 120c along the third direction Z and form the sampling response output signals 11' propagating toward the respective detectors 220a, 220b and 220c that vertically correspond to the sampling apertures 120a, 120b and 120c. Each of the detectors 220a, 220b and 220c detects whether a sampling response output signal has passed through a corresponding one of the sampling apertures 120a, 120b and 120c, thereby identifying whether one of the macromolecules having a corresponding size is present in the specific one of the sampling apertures 120a, 120b and 120c.

In this embodiment, the detectors are photoelectric detectors that can convert light signals into electric signals. Preferably, the detectors are semiconductor photoelectric detectors. More preferably, each of the photoelectric detectors includes at least a photoelectric diode having a light-receiving surface facing toward a corresponding one of the sampling apertures.

Figure 3:
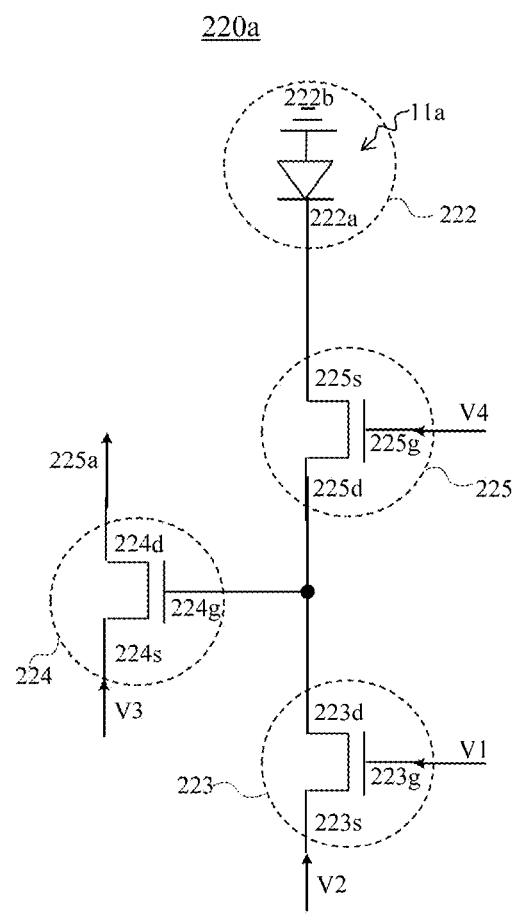
FIG. 3 is a schematic illustrating a detector according to one embodiment of the present invention.

With the detector 220a as an example, as shown in FIG. 3, the detector 220a includes a photoelectric diode 222. The photoelectric diode 222 has a light-receiving surface facing toward the sampling aperture 120a in order to receive the sampling response output signal 11a. According to this embodiment, using the photoelectric diodes provides the advantages as follows: compatibility with the fabrication of the semiconductor material-based substrates; simplification of the steps of the fabrication process; and high feasibility. In other embodiment, instead of the photoelectric diodes, other photoelectric devices, such as photoelectric sensors, other materials exhibiting changes in electric properties upon being irradiated by light, etc. may be used.

Preferably, the detector 220a further includes a first switching transistor 223 and a second switching transistor 224. The first switching transistor 223 has a drain 223d coupled to a first end 222a of the photoelectric diode 222. The second end 222b of the photoelectric diode 222 is connected to a common ground. The first switching transistor 223 further has a gate 223g coupled to a reset control signal V1 and a source 223s receiving a reset input signal V2. According to the basic principles of a source follower amplification circuit, the second switching transistor 224 has a gate 224g coupled to the first end 222a of the photoelectric diode 222 and the drain 223d of the first switching transistor 223, a source 224s coupled to an amplified input signal V3, and a drain 224d outputting the detection output signal 225a. Under the control of the first switching transistor 223, the second switching transistor 224 receives a signal from the first end 222a of the photoelectric diode 222 and outputs the detection output signal 225a.

Preferably, the detector 220a further includes a third switching transistor 225. The third switching transistor 225 has a source 225s coupled to the first end 222a of the photoelectric diode 222, a gate 225g coupled to an inductive conducting and reset control signal V4, and a drain 225d coupled to both the drain 223d of the first switching transistor 223 and the gate 224g of the second switching transistor 224. The third switching transistor 225 is configured to reset the detector 220a.

In this embodiment, the detection source signals 11 are light signals and the detectors 220a, 220b and 220c are photoelectric detectors. In other embodiments, however, the detection source signals 11 may also be implemented as infrared signals or radio-frequency (RF) signals, and the detectors 220a, 220b and 220c are accordingly thermal radiation detectors and RF signal detectors. The detectors 220a, 220b and 220c may also be capable of detecting whether the macromolecules are present in the sampling apertures 120a, 120b and 120c, which are also fall within the scope of the invention.

As shown in FIG. 1, in this embodiment, the first substrate 100 and the second substrate 200 are attached to each other using adhesive pad(s) 190 such that the gap 195 is formed between the sampling apertures 120a, 120b and 120c and the detectors 220a, 220b and 220c. The gap 195 is conducive to the prevention of detection errors. For example, any macromolecule that can pass through a sampling aperture in the first substrate 100 will drop into the gap 195 rather than being clogged in the sampling aperture.

Alternatively, the apparatus 1 for detecting macromolecules in a biological fluid may include a plurality of separate adhesive pads 190. As shown in FIG. 1, in this embodiment, the apparatus 1 includes two stripe-shaped adhesive pads 190 respectively disposed on two sides of the entire of the sampling apertures 120a, 120b and 120c to avoid forming an obstacle between the sampling apertures 120a, 120b and 120c and the detectors 220a, 220b and 220c. It is a matter of course that the adhesive pads 190 may also be deployed at other areas between the first substrate 100 and the second substrate 200. The adhesive pads 190 may each assume a column-like shape, as long as they will not block the propagation of signals between the sampling apertures 120a, 120b and 120c and the detectors 220a, 220b and 220c.

In other embodiment, the apparatus 1 for detecting macromolecules in a biological fluid may include a continuous adhesive pad 190 having an opening formed therein. For example, the adhesive pad 190 may be an annulus and the opening is the central opening of the annulus. The adhesive pad 190 may have one side connected with the periphery of the first substrate 100 and the other side connected with the periphery of the second substrate 200, thereby forming the gap 195 within the area of the opening. It is a matter of course that the adhesive pad 190 may have other shape than the annulus or have a plurality of openings, which are also within the scope of the invention as long as they will not form an obstacle between the sampling apertures 120a, 120b and 120c and the detectors 220a, 220b and 220c.

In addition, while the first substrate 100 and the second substrate 200 have been described above as being connected with the adhesive pad(s) 190, the present invention is not limited to this regard as the first substrate 100 and the second substrate 200 may also be fixed at relative positions by brackets, which is also within the scope of the invention as long as the gap 195 can be formed between the sampling apertures 120a, 120b and 120c and the detectors 220a, 220b and 220c.

A collection analysis module 300 may be connected to the detectors 220a, 220b and 220c. The collection analysis module 300 is configured to receive the detection output signals 225a, 225b and 225c and identify molecular properties of the macromolecules based on the detection output signals 225a, 225b and 225c. As the collection analysis module 300 can be understood by those of ordinary skill in this art, detailed description of it will be omitted herein.

For example, when light is incident on the first substrate 100, portions of the light entering ones of the sampling apertures filled with the macromolecules will be absorbed or attenuated by the macromolecules, and the corresponding ones of the detectors will receive the attenuated light portions and produce detection output signals carrying information indicative of the attenuation. In addition, portions of the light entering ones of the sampling apertures not filled with any macromolecule will completely pass through the sampling apertures without being attenuated, and the corresponding ones of the detectors will receive the non-attenuated light portions and produce detection output signals containing information indicative of the non-attenuation. The collection analysis module 300 will then receive and analyze all the detection output signals output from the detectors to identify the sampling apertures filled with the macromolecules and to identify the types of the molecules contained in portions of the fluids flowing through these sampling apertures based on their diameters. In other embodiments, the collection analysis module may not be included, and the identification of the sampling apertures filled with the macromolecules may be accomplished in other manners, for example, by indicator lamps or manual calculation. This can be understood by those skilled in the art, and detailed description will thus be omitted.

A method for detecting macromolecules in a biological fluid in accordance with an embodiment of the present invention will be described in detail below with reference to FIGS. 4 to 7.

Figure 4:
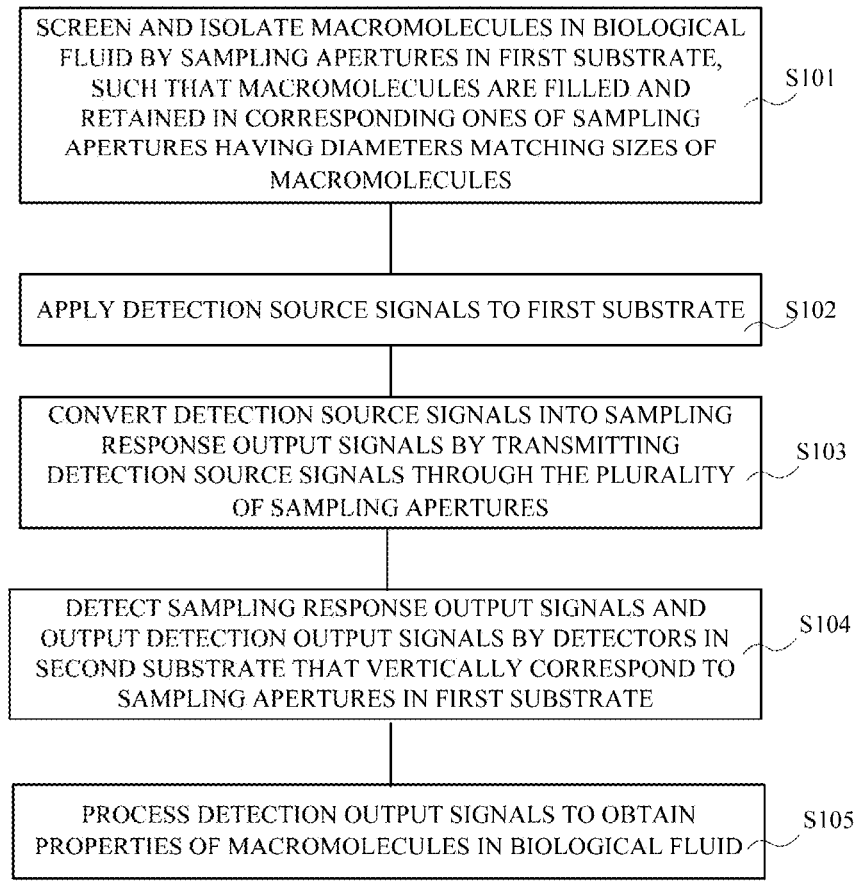
FIG. 4 is a flowchart graphically illustrating a method for detecting macromolecules in a biological fluid according to one embodiment of the present invention.
Figure 5:
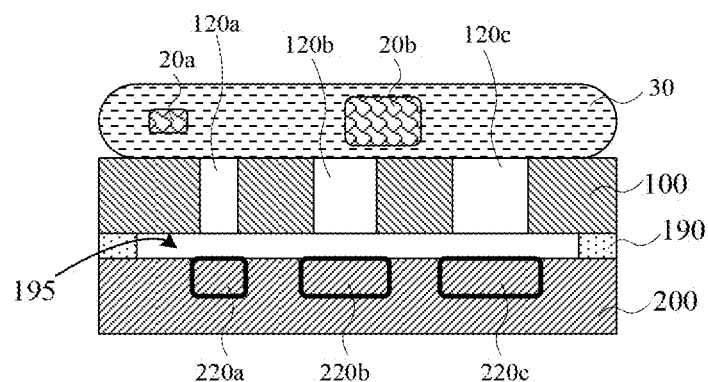
FIGS. 5 to 7 are cross-sectional views of a detection system used in a method for detecting macromolecules in a biological fluid according to one embodiment of the present invention.

In step S101, as shown in FIG. 4, the molecules in the fluid are screened and isolated by means of the plurality of sampling apertures 120a, 120b and 120c in the first substrate 100. Referring to FIG. 5, the fluid 30 may be placed on the side of the first substrate 100 opposite to the second substrate 200. In this embodiment, the fluid 30 is a biological fluid containing molecules 20a and 20b. The molecules 20a and 20b are DNA molecules having different sizes and the DNA molecules are in a free state in the fluid 30.

Figure 6:
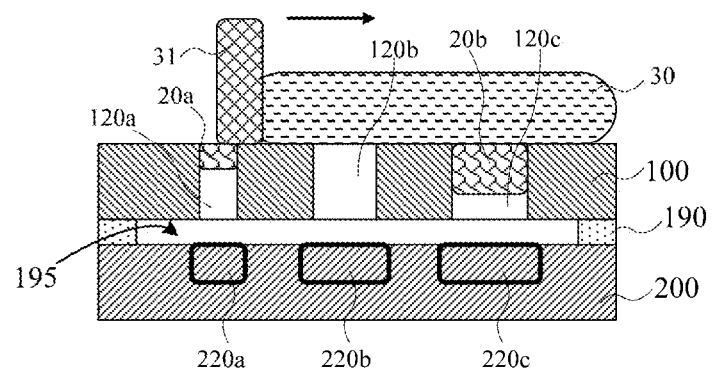

The size of the macromolecule 20a is exactly equal to a diameter of the sampling aperture 120a, and the size of the macromolecule 20b is exactly equal to a diameter of the sampling aperture 120b. Optionally, a scraper 31 may be used to shave the side of the first substrate 100 opposite to the second substrate 200. As a result, a pressure is formed, under which the macromolecule 20a is filled and thereby retained in the sampling aperture 120a and the macromolecule 20b is filled and thereby retained in the sampling aperture 120c, as shown in FIG. 6, thus accomplishing the screening of the fluid 30.

Afterward, temperature of the first substrate 100 and the macromolecules retained in the sampling apertures thereof is controlled in the range of from −196° C. to 99° C., for example, −190° C., −180° C., −150° C., −120° C., −100° C., −50° C., 0° C., 10° C., 20° C., 50° C., 80° C. or 90° C.

For example, the first substrate 100 may be heated to evaporate the volatile solvent in which the screened macromolecules 20a and 20b are dissolved such that, only the macromolecules 20a and 20b remain in the respective sampling apertures 120a and 120c and no fluid 30 is not remained in the sampling apertures 120a and 120c. This is conducive to improving the accuracy of the detection.

In addition, the first substrate 100 may also be chilled to fix the solution (i.e., the fluid 30) containing the screened macromolecules 20a and 20b, as well as the macromolecules 20a and 20b themselves, within the respective sampling apertures 120a and 120c, thereby achieving the retention of the macromolecules 20a and 20b in the respective sampling apertures 120a and 120c.

The heating or chilling of the first substrate 100 may be accomplished either by directly heating or chilling the first substrate 100 or by heat conduction with the second substrate 200 that is heated or chilled. The most direct and simple heating method is to apply an electric current to the first substrate 100 or the second substrate 200. For example, an in-situ temperature measuring device (e.g., a silicon-based semiconductor temperature-sensing device) may be deployed on the first substrate 100 or the second substrate 200 and energized to heat the first substrate 100 or the second substrate 200, so that the sample carrier substrate, i.e., the first substrate 100, may be heated to a temperature near to 100° C. (for facilitating the evaporation of the solution). A relatively direct chilling method is to utilize an external cooler. For example, a thermoelectric cooler (TEC) may be attached to the second substrate 200, or liquid nitrogen may be used for a local region required to be cooled to a temperature lower than −100° C. (with −196° C. as the maximum achievable temperature).

Figure 7:
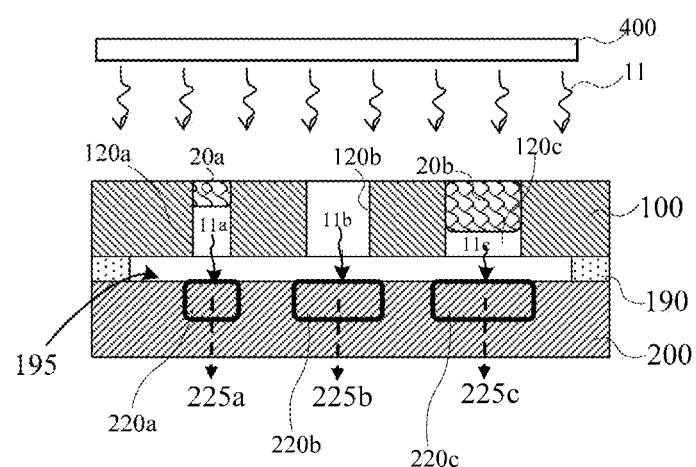

In step S102, detection source signals are applied to the first substrate 100. In this embodiment, as shown in FIG. 7, the detection source signals 11 are applied by the detection source signal transmission module 400 from the side of the first substrate 100 opposite to the second substrate 200 toward the sampling apertures 120a, 120b and 120c.

In step 103, the detection source signal passing through each of the sampling apertures produces a sampling response output signal indicating whether there is a corresponding macromolecule therein. Referring to FIG. 7, in this embodiment, as the sampling apertures 120a and 120c contain the respective macromolecules 20a and 20b, the ones of the detection source signals 11 passing through the sampling apertures 120a and 120c are attenuated. On the contrary, the one of the detection source signals 11 transmitting through the sampling aperture 120b is not attenuated. As a result, different signal responses (11a, 11b and 11c) are formed, .e.g., different attenuated sampling response output signals 11a, 11b and 11c.

In step 104, the detectors in the second substrate vertically corresponding to the sampling apertures in the first substrate detect the sampling response output signals and output detection output signals. In this embodiment, as shown in FIG. 7, the detectors 220a, 220b and 220c receive the sampling response output signals 11a, 11b and 11 c from the corresponding sampling apertures 120a, 120b and 120c and convert the sampling response output signals 11a, 11b and 11c into detection output signals 225a, 225b and 225c.

Lastly, in step 105, the detection output signals are processed to identify properties of the macromolecules in the biological fluid. In this embodiment, the collection analysis module 300 receives the detection output signals 225a, 225b and 225c and identifies based thereon molecular properties of the macromolecules. For example, in this embodiment, the collection analysis module 300 can ascertain that there are two differently sized macromolecules in the fluid 30 and further obtain the sizes of the macromolecules.

In summary, in this embodiment, the first substrate 100 serves as a macromolecular sieve to screen and isolate the macromolecules 20a and 20b in the fluid 30 by means of the sampling apertures 120a, 120b and 120c. After the macromolecules 20a and 20b are retained in the correspondingly-sized sampling apertures 120a and 120c, the second substrate 200 functions as a detector to detect each of the sampling apertures 120a, 120b and 120c to find whether there is one of the macromolecules present therein and output responsive detection output signals 225a, 225b and 225c. The collection analysis module 300 receives the detection output signals 225a, 225b and 225c and identifies molecular properties of the macromolecules based on the detection output signals 225a, 225b and 225c. The inventive apparatus 1 for detecting macromolecules in a biological fluid has high integration and simple manufacturability, while the inventive method is easy to use.

In addition, apparatuses and methods according to the present invention are not limited to use in the detection of macromolecules in a biological fluid, because the apparatuses may also be used in combination with similar methods in the screening and isolation of particles suspended in a liquid and in ascertainment of the composition of the particles. In addition, the macromolecules in a biological fluid are not limited to DNA macromolecules, because any macromolecules in a biological fluid can be detected using the apparatuses and methods according to the present invention.

Further, the apparatus may also employ thermal radiation signals or RF signals as the detection source signals, and accordingly, the detectors may be implemented as thermal radiation detectors or RF signal detectors. In this case, the apparatus may perform similar sampling, detection, signal amplification and outputting processes to obtain the properties of the macromolecules in the biological fluid.

While the invention has been described with reference to the foregoing embodiments, it should be understood that these disclosed embodiments are exemplary and illustrative, not intended to limit the invention to only the scope of the disclosed embodiments. In addition, it will be understood by those skilled in the art that the present invention is not limited to the disclosed embodiments and various changes and modifications can be made therein in light of the above teachings. Therefore, it is intended that all such changes and modifications fall within the scope of the invention as defined by the appended claims and their equivalents.

What is claimed is:

1. A method for detecting macromolecules in a biological fluid, using an apparatus for detecting the macromolecules in the biological fluid, the apparatus comprising: a first substrate, comprising a plurality of sampling apertures, at least some of the plurality of sampling apertures having different diameters, the plurality of sampling apertures configured to screen and isolate the macromolecules in the biological fluid; a second substrate, stacked with the first substrate and comprising a plurality of detectors vertically arranged in correspondence with positions of the plurality of sampling apertures, each of the plurality of detectors configured to detect whether one of the macromolecules is present in a corresponding one of the plurality of sampling apertures and produce a detection output signal; and an in-situ temperature measuring device configured to be energized to heat the first substrate or the second substrate, the method comprising:

screening and isolating the macromolecules in the biological fluid by means of the plurality of sampling apertures in the first substrate, such that the macromolecules are filled and retained in corresponding ones of the plurality of sampling apertures having diameters matching sizes of the macromolecules;

applying detection source signals to the first substrate;

converting the detection source signals into sampling response output signals by transmitting the detection source signals through the plurality of sampling apertures;

detecting the sampling response output signals and outputting detection output signals by the plurality of detectors in the second substrate that vertically correspond to the plurality of sampling apertures in the first substrate;

processing the detection output signals to obtain properties of the macromolecules in the biological fluid; and performing a temperature control on the first substrate and the macromolecules retained in the plurality of sampling apertures in the first substrate.

2. The method of claim 1, wherein the temperature control performed on the first substrate and the macromolecules retained in the plurality of sampling apertures in the first substrate is accomplished by increasing or decreasing a temperature of the second substrate.

3. The method of claim 1, wherein the temperature control performed on the first substrate and the macromolecules retained in the plurality of sampling apertures in the first substrate is accomplished by directly increasing or decreasing a temperature of the first substrate.

4. The method of claim 1, wherein the temperature of the first substrate and the macromolecules retained in the plurality of sampling apertures ranges from $-196°$ C. to $99°$ C.

* * * * *